United States Patent
Scavuzzo et al.

(10) Patent No.: US 10,562,873 B1
(45) Date of Patent: Feb. 18, 2020

(54) METHODS OF PRODUCING GLYCIDYL NITRATE

(71) Applicant: Northrop Grumman Innovation Systems, Inc., Plymouth, MN (US)

(72) Inventors: Joseph J. Scavuzzo, Ogden, UT (US); Melissa L. Mileham, Providence, UT (US)

(73) Assignee: Northrop Grumman Innovation Systems, Inc., Plymouth, MN (US)

( * ) Notice: Subject to any disclaimer, the term of this patent is extended or adjusted under 35 U.S.C. 154(b) by 0 days.

(21) Appl. No.: 16/213,130

(22) Filed: Dec. 7, 2018

(51) Int. Cl.
*C07D 301/02* (2006.01)
*C06B 25/00* (2006.01)
*B01J 8/18* (2006.01)

(52) U.S. Cl.
CPC .......... *C07D 301/02* (2013.01); *B01J 8/1872* (2013.01); *C06B 25/00* (2013.01)

(58) Field of Classification Search
CPC ....... C07D 301/02; B01J 8/1872; C06B 25/00
USPC ........................................................ 549/518
See application file for complete search history.

(56) References Cited

U.S. PATENT DOCUMENTS

| | | | |
|---|---|---|---|
| 5,089,652 A * | 2/1992 | Sohara | C07C 201/02 558/480 |
| 6,362,311 B1 | 3/2002 | Highsmith et al. | |
| 6,870,061 B2 | 3/2005 | Highsmith et al. | |
| 8,536,366 B2 * | 9/2013 | Braune | B01J 19/0093 210/638 |
| 2007/0287852 A1 * | 12/2007 | Antes | B01J 19/0093 558/480 |

OTHER PUBLICATIONS

Scavuzzo; Paper tiltled "Microfluidic Synthesis of Energetic Materials" Abstract # 20271, 9 pages. NDIA 2018 IM & EM Technology Symposium, Portland OR; Apr. 25, 2018. Downloaded Feb. 28, 2019 from https://ndiastorage.blob.core.usgovcloudapi.net/ndia/2018/imem/20271_Scavuzzo_Paper.pdf (Year: 2018).*
Scavuzzo; Presentation tiltled "Microfluidic Synthesis of Energetic Materials" Abstract # 20271, 15 pages. NDIA 2018 IM & EM Technology Symposium, Portland OR; Apr. 25, 2018. Downloaded Feb. 28, 2019 from https://ndiastorage.blob.core.usgovcloudapi.net/ndia/2018/imem/20271_Scavuzzo_Presentation.pdf (Year: 2018).*
Movsisyan; Chem. Soc. Rev., 2016, 45, 4892-4928 . (Year: 2016).*
Kulkarni; Beilstein J. Org. Chem. 2014, 10, 405-424. (Year: 2014).*
Geyer; Chem. Eur. J. 2006, 12, 8434-8442. (Year: 2006).*
Sun; Process Safety Progress 2016, 35, 365-373. (Year: 2016).*

(Continued)

*Primary Examiner* — Daniel R Carcanague
(74) *Attorney, Agent, or Firm* — TraskBritt (57) ABSTRACT

Methods of producing glycidyl nitrate. The method comprises reacting glycerol and nitric acid in a microfluidic reactor to form a nitrated glycerol compound. The microfluidic reactor comprises a reaction volume of the microfluidic reactor of less than about 20 ml and an inner diameter of a reaction channel of the microfluidic reactor of less than or equal to about 1000 μm. The nitrated glycerol compound is reacted with a base in the microfluidic reactor to form glycidyl nitrate. Additional methods of producing glycidyl nitrate are also disclosed.

18 Claims, 2 Drawing Sheets

(56) References Cited

OTHER PUBLICATIONS

Li; Chemical Engineering & Processing: Process Intensification 117 (2017) 179-185. (Year: 2017).*
Syrris, Applications "What is Flow Chemistry and What are the Benefits of Flow Chemistry", https://syrris.com/applications/flow-chemistry-applications, web page last accessed Dec. 5, 2018 (17 pages).
Syrris, "Flow Chemistry Reactors", https://syrris.com/solutions/flow-chemistry, web page last accessed Dec. 5, 2018 (4 pages).
Elvira et al, "The past, present and potential for microfluidic reactor technology in chemical synthesis" Review Article, Published Online: Oct. 13, 2013; DOI: 10.1038/NCHEM.1752, (11 pages).
Chemtrix, "Flow Chemistry Technology", https://www.chemtrix.com/flow-chemistry, web page last accessed Dec. 5, 2018 (2 pages).
Chemtrix, "Flow Chemistry Equipment", https://www.chemtrix.com/products, web page last accessed Dec. 5, 2018 (1 page).

* cited by examiner

METHODS OF PRODUCING GLYCIDYL NITRATE

TECHNICAL FIELD

Embodiments of the disclosure relate generally to methods of producing an energetic material. More particularly, embodiments of the disclosure relate to methods of producing glycidyl nitrate (GLYN) by a microfluidic process.

BACKGROUND

Glycidyl nitrate (GLYN) is an energetic precursor that is used to produce poly(glycidyl nitrate) (PGN), an energetic polymer. The PGN is used as a polymer in a binder system for explosives or propellants. Producing GLYN is a hazardous process that includes two exothermic chemical reactions and generates trinitroglycerol (NG) as a byproduct. Glycerol is nitrated to form a dinitroglycerol (DNG) compound, which is cyclized to form the GLYN. During the nitration reaction, process conditions are closely controlled to prevent runaway reactions. Extensive cooling is also utilized to control the reaction. The thermally unstable oxirane ring of GLYN also contributes to the hazards of the process.

Conventionally, GLYN has been produced by batch or continuous batch processes. The batch processes have a low capital cost and a reasonable ability to scale up. However, the hazards associated with the batch processes are high due to the large volumes and amounts of reagents, intermediates, and reaction products used in large scale production. The conventional processes also use large volumes of solvent, such as dichloromethane (DCM), that subsequently need to be disposed of The continuous batch processes have a high capital cost and a reasonable ability to scale up, along with a high likelihood of hazards due to the large volumes and amounts of reagents, intermediates, and reaction products used for large scale production. Mitigating the hazards in the batch and continuous batch processes has made conventional processes of producing GLYN prohibitively expensive. The large scale production of GLYN is, therefore, not only dangerous but also expensive.

BRIEF SUMMARY

In accordance with some embodiments described herein, a method of producing glycidyl nitrate (GLYN) is disclosed. The method comprises reacting glycerol and nitric acid in a microfluidic reactor to form a nitrated glycerol compound. The microfluidic reactor comprises a reaction volume of the microfluidic reactor of less than about 20 ml and an inner diameter of a reaction channel of the microfluidic reactor of less than or equal to about 1000 µm. The nitrated glycerol compound is reacted with a base in the microfluidic reactor to form GLYN.

In accordance with other embodiments, another method of producing glycidyl nitrate (GLYN) is disclosed. The method comprises introducing glycerol and nitric acid into a first reaction channel of a microfluidic reactor. The microfluidic reactor comprises a reaction volume of the microfluidic reactor of less than about 20 ml and an inner diameter of a reaction channel of the microfluidic reactor of less than or equal to about 1000 µm. The glycerol and nitric acid are reacted in the first reaction channel to form a nitrated glycerol compound. The nitrated glycerol compound is reacted with sodium hydroxide in a second reaction channel of the microfluidic reactor to form GLYN, which is recovered.

In accordance with other embodiments, yet another method of producing glycidyl nitrate (GLYN) is disclosed. The method comprises continuously reacting glycerol and nitric acid in a first reaction channel of a microfluidic reactor to form a dinitroglycerol (DNG) compound. The microfluidic reactor comprises a reaction volume of the microfluidic reactor of less than about 20 ml and an inner diameter of a reaction channel of the microfluidic reactor of less than or equal to about 1000 µm. The DNG compound is continuously reacted with sodium hydroxide in a second reaction channel of the microfluidic reactor to form GLYN, which is recovered.

DETAILED DESCRIPTION

Methods of producing glycidyl nitrate (GLYN) are disclosed. The GLYN is produced by a continuous process using a microfluidic reactor (e.g., a flow reactor) having a continuous flow reaction channel with an inner diameter of less than or equal to about 1000 µm and a reaction volume of less than or equal to about 20 ml. Glycerol is reacted with a nitrating agent to form a nitrated glycerol compound, which is subjected to an intramolecular condensation in the presence of a base to produce the GLYN. The nitration reaction and the intramolecular condensation reaction are conducted in the microfluidic reactor, enabling the GLYN to be produced continuously. The GLYN is produced by a safer process than conventional batch or continuous processes. The conversion from glycerol to GLYN according to embodiments of the disclosure is comparable to conventional batch or continuous processes of producing GLYN.

As used herein, the singular forms "a," "an," and "the" are intended to include the plural forms as well, unless the context clearly indicates otherwise.

As used herein, the term "about" or "approximately" in reference to a numerical value for a particular parameter is inclusive of the numerical value and a degree of variance from the numerical value that one of ordinary skill in the art would understand is within acceptable tolerances for the particular parameter. For example, "about" or "approximately" in reference to a numerical value may include additional numerical values within a range of from 90.0 percent to 110.0 percent of the numerical value, such as within a range of from 95.0 percent to 105.0 percent of the numerical value, within a range of from 97.5 percent to 102.5 percent of the numerical value, within a range of from 99.0 percent to 101.0 percent of the numerical value, within a range of from 99.5 percent to 100.5 percent of the numerical value, or within a range of from 99.9 percent to 100.1 percent of the numerical value.

As used herein, the term "and/or" includes any and all combinations of one or more of the associated listed items.

As used herein, spatially relative terms, such as "beneath," "below," "lower," "bottom," "above," "upper," "top," "front," "rear," "left," "right," and the like, may be used for ease of description to describe one element's or feature's relationship to another element(s) or feature(s) as illustrated in the figures. Unless otherwise specified, the spatially relative terms are intended to encompass different orientations of the materials in addition to the orientation depicted in the figures. For example, if materials in the figures are inverted, elements described as "below" or "beneath" or "under" or "on bottom of" other elements or features would then be oriented "above" or "on top of" the other elements or features. Thus, the term "below" can encompass both an orientation of above and below, depending on the context in which the term is used, which will be evident to one of ordinary skill in the art. The materials may be otherwise oriented (e.g., rotated 90 degrees, inverted, flipped, etc.) and the spatially relative descriptors used herein interpreted accordingly.

As used herein, the terms "comprising," "including," "containing," "characterized by," and grammatical equivalents thereof are inclusive or open-ended terms that do not exclude additional, unrecited elements or method steps, but also include the more restrictive terms "consisting of" and "consisting essentially of" and grammatical equivalents thereof.

As used herein, the term "configured" refers to a size, shape, material composition, and arrangement of one or more of at least one structure and at least one apparatus facilitating operation of one or more of the structure and the apparatus in a pre-determined way.

As used herein, the term "may" with respect to a material, structure, feature or method act indicates that such is contemplated for use in implementation of an embodiment of the disclosure and such term is used in preference to the more restrictive term "is" so as to avoid any implication that other, compatible materials, structures, features and methods usable in combination therewith should or must be excluded.

As used herein, the term "microfluidic reactor" means and includes a vessel (e.g., a reactor) configured to conduct chemical reactions under geometrically constrained conditions. The reactor includes a reaction channel having internal dimensions on the μm scale, such as between about 1 μm and about 1000 μm, and a reaction volume of less than or equal to about 20 ml.

For example, the reaction channel may have an inner diameter of less than or equal to about 1000 μm.

As used herein, the term "reaction solution" means and includes a combination of reagents (e.g., the glycerol and nitrating agent, the nitrated glycerol compound and base) in an optional solvent. The reagents (e.g., the glycerol and nitrating agent, the nitrated glycerol compound and base) may be substantially soluble in the optional solvent or may be substantially miscible with one another.

As used herein, the term "reaction volume" means and includes a volume of a reaction channel of the microfluidic reactor within which the reaction(s) is conducted.

As used herein, the term "resonance time" means and includes a total time the reaction solution including the reagents is in the microfluidic reactor. The resonance time is a function of the reaction volume of the microfluidic reactor and of a flow rate that the reaction solution is flowed through the microfluidic reactor. The resonance time corresponds to the amount of time for the reaction volume to move through the microfluidic reactor.

As used herein, the term "substantially," in reference to a given parameter, property, or condition, means to a degree that one of ordinary skill in the art would understand that the given parameter, property, or condition is met with a small degree of variance, such as within acceptable manufacturing tolerances. By way of example, depending on the particular parameter, property, or condition that is substantially met, the parameter, property, or condition may be at least 90.0% met, at least 95.0% met, at least 99.0% met, or even at least 99.9% met.

The following description provides specific details, such as reagents, reagent amounts, and reaction conditions in order to provide a thorough description of embodiments of the disclosure. However, a person of ordinary skill in the art will understand that the embodiments of the disclosure may be practiced without employing these specific details. Indeed, the embodiments of the disclosure may be practiced in conjunction with conventional processes employed in the industry. In addition, the description provided below does not form a complete process flow for producing the GLYN. Only those process acts necessary to understand the embodiments of the disclosure are described in detail below. Additional acts may be performed by conventional techniques. Also note, any drawings accompanying the application are for illustrative purposes only, and are thus not drawn to scale. Additionally, elements common between figures may retain the same numerical designation.

The glycerol is nitrated in a first reaction channel of the microfluidic reactor to form the nitrated glycerol compound and an intramolecular ring closure is conducted in a second reaction channel of the microfluidic reactor and on the nitrated glycerol compound according to the following reaction scheme:

The nitration reaction and the intramolecular condensation reaction may be conducted in series in the microfluidic reactor. The glycerol is nitrated with the nitrating agent, such as nitric acid ($HNO_3$), to form the nitrated glycerol compound, such as a dinitroglycerol (DNG) compound. The DNG compound may include, but is not limited to, 1,2-dinitroglycerol, 1,3-dinitroglycerol, or combinations thereof. While specific examples herein disclose using nitric acid as the nitrating agent, other nitrating agents may be used, such as a combination of sulfuric acid and nitric acid, acetyl nitrate, a nitronium ion salt, etc.

Other nitrated glycerol compounds, such as a mononitroglycerol (MNG) compound or trinitroglycerol (NG), may be formed as byproducts during the nitration reaction. To achieve a high yield of GLYN, the amount of DNG compound produced may be maximized (e.g., a major reaction product of the nitration reaction), with trace amounts or substantially no MNG compound or NG produced. The MNG compound, if present, reduces the purity of the resulting GLYN and affects subsequent polymerization of the GLYN. The NG, if present, increases the risk of hazards associated with the nitration reaction, as well as reduces the purity of the resulting GLYN. Reaction temperature, nitric acid concentration, and resonance time may be adjusted to produce the DNG compound as the major reaction product of the nitration reaction. If, however, the MNG compound and/or NG are produced, these byproducts may optionally be removed by conventional techniques to increase the purity of the DNG compound.

The nitric acid used as the nitrating agent may be concentrated nitric acid (98%) or a nitric acid solution. The nitric acid solution includes the nitric acid and a solvent, such as dichloromethane (DCM). A ratio of the solvent to the nitric acid (solvent:nitric acid) may range from about 0.01:1 to about 1:1. In some embodiments, concentrated nitric acid is used as the nitrating agent. It was found that the GLYN produced in accordance with embodiments of the disclosure was produced without using a solvent in the nitration reaction. In other words, the nitration reaction may be a solventless process. Given the exothermic nature of the reaction, it was unexpected for the nitration reaction to be conducted without using a solvent. In addition to simplifying the reaction, eliminating the solvent is advantageous because safety is increased and costs associated with solvent disposal are reduced. This is in contrast to conventional batch and continuous processes of producing GLYN, which utilize large volumes of solvent to dilute the nitric acid and to dissipate heat generated by the exothermic reaction. In these conventional batch and continuous processes, the solvent accounts for a large volume of the nitration reaction and, therefore, solvent disposal costs are high.

An excess of the nitric acid may be used relative to the glycerol. A ratio of the nitric acid to glycerol (nitric acid: glycerol) may range from about 4.0:0.5 to about 4.0:1.5, such as from about 4.0:0.5 to about 4.0:1.2, from about 4.0:0.6 to about 4.0:1.0, from about 4.0:0.6 to about 4.0:0.9, from about 4.0:0.6 to about 4.0:0.8, from about 4.0:0.6 to about 4.0:0.75, or from about 4.0:0.6 to about 4.0:0.7. In some embodiments, the ratio of nitric acid to glycerol is about 4.0:0.68.

The glycerol and nitric acid may be reacted in the first reaction channel of the microfluidic reactor for an amount of time sufficient to form the nitrated glycerol compound. The time may range from about 1 minute to about 40 minutes, such as from about 1 minute to about 35 minutes, from about 1 minute to about 30 minutes, from about 2 minutes to about 25 minutes, from about 5 minutes to about 25 minutes, from about 10 minutes to about 25 minutes, from about 15 minutes to about 25 minutes, from about 20 minutes to about 25 minutes, or from about 15 minutes to about 20 minutes. In some embodiments, the nitration reaction time (e.g., resonance time) is about 21 minutes.

The glycerol and nitric acid may be reacted at a temperature ranging from about 15° C. to about 30° C., such as from about 15° C. to about 25° C., from about 15° C. to about 20° C., from about 20° C. to about 30° C., or from about 20° C. to about 25° C. In some embodiments, the nitration reaction is conducted at a reaction temperature of about 20° C. In other embodiments, the nitration reaction is conducted at a reaction temperature of about 21° C. In yet other embodiments, the nitration reaction is conducted at a reaction temperature of about 22° C. By controlling the temperature of the nitration reaction, the DNG compound may be produced at a higher purity by decreasing side reactions that produce the MNG compound or NG.

The glycerol and nitric acid may be introduced into the first reaction channel of the microfluidic reactor at a flow rate sufficient for the glycerol and nitric acid to react to substantial completion in the reaction channel. The flow rate may be within a range of from about 0.05 ml/minute to about 6.25 ml/minute, from about 0.10 ml/minute to about 6.00 ml/minute, from about 0.10 ml/minute to about 5.50 ml/minute, from about 0.10 ml/minute to about 5.00 ml/minute, from about 0.10 ml/minute to about 4.50 ml/minute, from about 0.10 ml/minute to about 4.00 ml/minute, from about 0.10 ml/minute to about 3.50 ml/minute, from about 0.10 ml/minute to about 3.00 ml/minute, from about 0.10 ml/minute to about 2.50 ml/minute, from about 0.10 ml/minute to about 2.00 ml/minute, from about 0.10 ml/minute to about 1.50 ml/minute, from about 0.10 ml/minute to about 1.25 ml/minute, from about 0.125 ml/minute to about 1.25 ml/minute, from about 0.15 ml/minute to about 1.25 ml/minute, from about 0.25 ml/minute to about 1.25 ml/minute, or from about 0.75 ml/minute to about 1.25 ml/minute. In some embodiments, the flow rate is 0.152 ml/minute. In other embodiments, the flow rate is 0.76 ml/minute. In yet other embodiments, the flow rate is 0.38 ml/minute. The flow rate of the glycerol and the nitric acid may be the same or may be different.

The resonance time of the reaction products of the nitration reaction may range from about 1.5 minutes to about 30.0 minutes, such as from about 2.0 minutes to about 25.0 minutes, from about 5.0 minutes to about 22.0 minutes, from about 10.0 minutes to about 22.0 minutes, from about 15.0 minutes to about 22.0 minutes, or from about 20.0 minutes to about 22.0 minutes. In some embodiments, the resonance time is 21.0 minutes. The glycerol and nitric acid may substantially completely react in about 20 minutes, such as between about 20 minutes and about 30 minutes. The short reaction time for the nitration reaction was unexpected relative to the reaction times of conventional glycerol nitration processes.

The nitration reaction may produce the DNG compound at a conversion of greater than or equal to about 50 mole percent (mol %), such as from about 50 mol % to about 85 mol %, from about 55 mol % to about 80 mol %, from about 60 mol % to about 80 mol %, from about 65 mol % to about 80 mol %, from about 65 mol % to about 75 mol %, or from about 70 mol % to about 80 mol %. In some embodiments, the DNG compound is produced at greater than or equal to about 70 mol %.

Following the nitration reaction, the DNG compound may be present in an acidic solution that includes nitric acid. The DNG compound in the acidic solution is exposed to a base in the second reaction channel of the microfluidic reactor to induce the intramolecular ring closure and form the GLYN. A concentration of the acidic solution of the DNG compound may range from about 1.0 M to about 3.0 M, such as from about 1.5 M to about 3.0 M, from about 2.0 M to about 3.0 M, from about 1.5 M to about 2.5 M, from about 1.5 M to about 2.0 M, or from about 2.0 M to about 2.5 M. In some embodiments, the acidic solution includes 2.48 M of the DNG compound. The base may include, but is not limited to, sodium hydroxide (NaOH), and a concentration of the sodium hydroxide may range from about 3.0 M to about 10.0 M, such as from about 5.0 M to about 8.0 M, from about 6.0 M to about 9.0 M, or from about 7.0 M to about 8.0 M. The sodium hydroxide may be an aqueous solution of sodium hydroxide. In some embodiments, the concentration of sodium hydroxide in the aqueous solution of sodium hydroxide is about 7.2 M.

A volume ratio of the DNG compound to the base may range from about 2.0:1 to about 4.5:1, such as from about 2.5:1 to about 4.0:1, from about 2.5:1 to about 3.5:1, or from about 2.5:1 to about 3.0:1. In some embodiments, the ratio of the DNG compound to the base is 2.7:1.

The DNG compound and the base may be reacted in the microfluidic reactor at a temperature of from about 10° C. to about 35° C., such as from about 10° C. to about 20° C., from about 10° C. to about 15° C., from about 15° C. to about 25° C., from about 15° C. to about 20° C., from about 20° C. to about 25° C., from about 20° C. to about 35° C., from about 25° C. to about 35° C., or from about 30° C. to about 35° C. In some embodiments, the temperature is about 14° C. In other embodiments, the temperature is about 20° C. In yet other embodiments, the temperature is about 22° C. In yet other embodiments, the temperature is about 32° C. Controlling the temperature of the intramolecular condensation reaction may produce the GLYN at a higher purity by decreasing side reactions.

The nitrated glycerol compound and the base may be introduced into the second reaction channel of the microfluidic reactor at a flow rate within a range of from about 0.05 ml/minute to about 10.00 ml/minute, from about 0.10 ml/minute to about 9.00 ml/minute, from about 0.50 ml/minute to about 8.00 ml/minute, from about 0.50 ml/minute to about 7.00 ml/minute, from about 0.50 ml/minute to about 6.50 ml/minute, from about 0.50 ml/minute to about 6.00 ml/minute, from about 0.50 ml/minute to about 5.50 ml/minute, from about 0.50 ml/minute to about 5.00 ml/minute, from about 0.05 ml/minute to about 2.50 ml/minute, from about 0.10 ml/minute to about 1.25 ml/minute, from about 0.125 ml/minute to about 1.25 ml/minute, from about 0.15 ml/minute to about 1.25 ml/minute, from about 0.25 ml/minute to about 1.0 ml/minute, from about 0.50 ml/minute to about 1.0 ml/minute, or from about 0.75 ml/minute to about 1.0 ml/minute. In some embodiments, the flow rate is between about 0.50 ml/minute and about 1.0 ml/minute. In other embodiments, the flow rate is between about 0.50 ml/minute and about 2.5 ml/minute.

The resonance time of the intramolecular condensation reaction may range from about 0.5 minutes to about 30.0 minutes, such as from about 2.0 minutes to about 25.0 minutes, from about 2.0 minutes to about 25.0 minutes, from about 5.0 minutes to about 25.0 minutes, from about 10.0 minutes to about 25.0 minutes, from about 15.0 minutes to about 25.0 minutes, from about 20.0 minutes to about 25.0 minutes, from about 1 minute to about 15 minutes, from about 2 minutes to about 10 minutes, from about 4 minutes to about 8 minutes, or from about 4 minutes to about 6 minutes. In some embodiments, the resonance time is about 1.2 minutes. In other embodiments, the resonance time is about 0.7 minutes. In comparison, converting the DGN compound to GLYN by conventional batch processes takes between 2 hours and 3 hours.

The GLYN is recovered from the microfluidic reactor and, optionally, subjected to purification before polymerizing the GLYN to form PGN. The conversion from glycerol to GLYN may be from about 50 mol % to about 90 mol %, such as from about 50 mol % to about 85 mol %, from about 50 mol % to about 80 mol %, from about 55 mol % to about 90 mol %, from about 60 mol % to about 90 mol %, from about 70 mol % to about 90 mol %, or from about 70 mol % to about 80 mol %. In some embodiments, the conversion from glycerol to GLYN is about 58 mol %. The purification of the GLYN may be conducted by conventional techniques. The PGN may be produced from the GLYN by conventional techniques.

Figure 1:
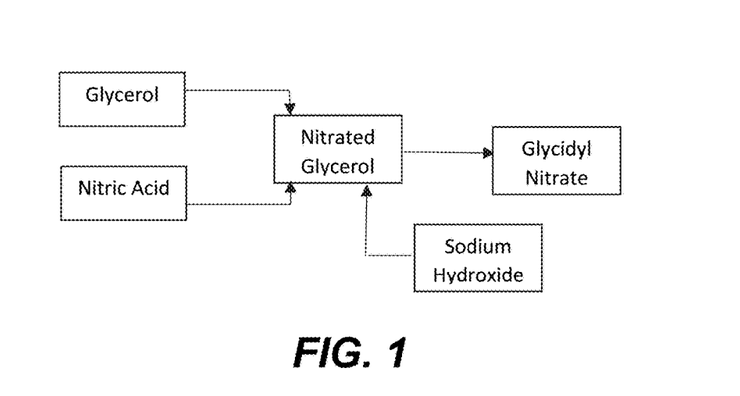
FIG. 1 is a process flow showing the production of GLYN in accordance with embodiments of the disclosure.
Figure 2:
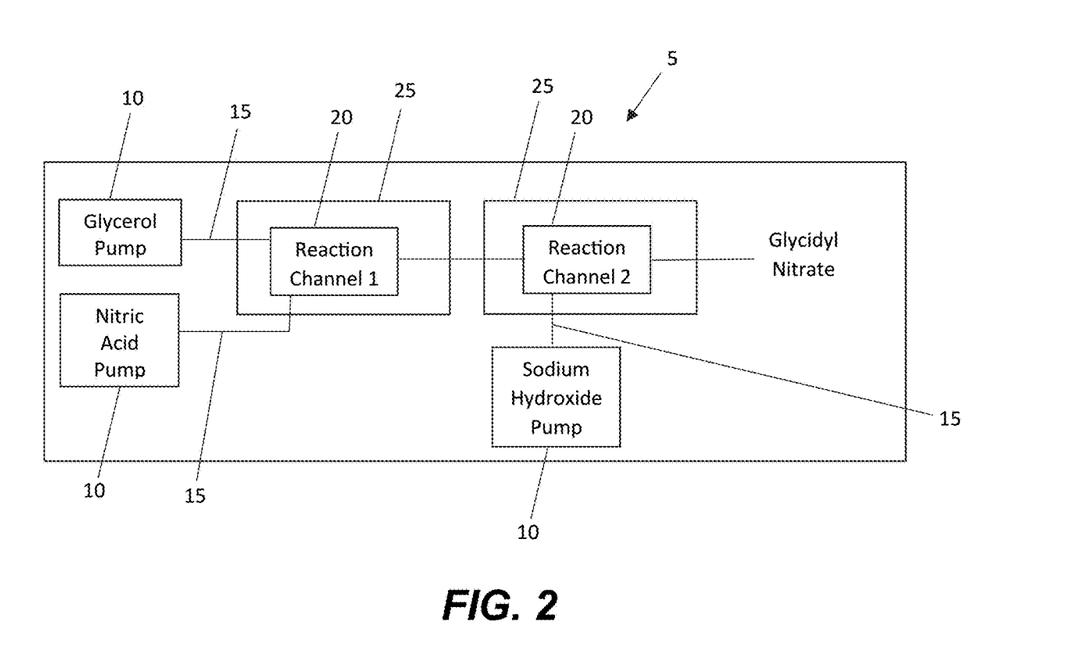
FIG. 2 is a schematic illustration of a microfluidic reactor configured to produce GLYN in accordance with embodiments of the disclosure.

The nitration reaction and the intramolecular ring closure reaction are conducted in a microfluidic reactor 5 that includes pumps 10, tubing 15, at least one reaction channel 20 (e.g., at least one resonance tube), and at least one temperature control system 25, as shown in FIG. 2. The microfluidic reactor 5 is configured to provide control of reagent flow rates, reagent mixing, reaction temperature, and resonance time. The components of the microfluidic reactor 5 are configured to be compatible with the reagents, optional solvents, and other process conditions of the reactions. Since the glycerol is reacted under acidic conditions and the DNG compound is reacted under basic conditions, the components of the microfluidic reactor 5 are substantially resistant to acidic and basic conditions. The reagents are continuously introduced into the reaction channels 20 of the microfluidic reactor 5 using the pumps 10 and the reactions occur in the reaction channels 20 at a desired reaction temperature. The reaction temperature is controlled by the temperature control systems 25, which also dissipate heat generated by the exothermic reactions.

The microfluidic reactor 5 may, for example, be configured as a glass chip or a glass plate having one or more reaction channels 20 etched in the glass. Internal dimensions of the reaction channels 20 may be between about 1 μm and about 1000 μm. The reaction volume of the microfluidic reactor 5 may depend on the dimensions (e.g., inner diameter, length) of the reaction channels 20 in which the nitration reaction and the intramolecular ring closure reaction are conducted. The reaction channels 20 of the microfluidic reactor 5 have a high surface area to bulk ratio to enable quick and efficient heat dissipation.

The pumps 10 are configured to introduce the reagents into the microfluidic reactor 5 at a desired flow rate, such as at a constant flow rate. Pumps 10 of varying sizes may be used to achieve the desired flow rate and reagent feed ratio. The glycerol and nitric acid are introduced into the microfluidic reactor 5 through inlets (not shown) and combined with mixing in the first reaction channel 20. The sodium hydroxide is introduced into the microfluidic reactor 5 through an inlet (not shown) and combined with the DNG compound in the second reaction channel 20. The reaction of the glycerol and nitric acid and the DNG compound and sodium hydroxide is based on the flow rate of the reagents through the microfluidic reactor 5 and the length of the first and second reaction channels 20. The flow rate of each of the reagents may be the same or may be different. Alternatively, the desired reagent feed ratio of each of the reagents may be achieved by dilution. Depending on the amount of GLYN to be produced, the pumps 10 may be syringe pumps or other conventional pumps.

The tubing 15 is configured to connect the components of the microfluidic reactor to one another, such as to connect the pumps 10 to the first and second reaction channels 20. The tubing 15 may, for example, be resistant to the acidic conditions of the nitration reaction and resistant to the basic conditions of the intramolecular condensation reaction. A material of the tubing 15 may, for example, be a polymeric material, a glass material, or a ceramic material. The tubing 15 may transport the glycerol, nitric acid, and sodium hydroxide from the pumps 10 to the first and second reaction channels 20. In some embodiments, the tubing 15 is polytetrafluoroethylene (PTFE) tubing. The tubing 15 may have an inner diameter of less than or equal to about 1 mm.

The reagents enter the first and second reaction channels 20 and are combined by mixing, such as by laminar flow mixing, diffusional mixing, etc. The reagents may be combined within a range from milliseconds to seconds due to the small reaction volume of the first and second reaction channels 20.

The microfluidic reactor 5 may include one or more reaction channels 20 configured to react the reagents (e.g., glycerol and nitric acid, DNG compound and base) to form the GLYN. The reaction channels 20 are substantially resistant to the reagents and optional solvents used in the reactions. The material of the reaction channels 20 may be resistant to the acidic conditions of the nitration reaction and the basic conditions of the intramolecular condensation reaction. The reaction channels 20 may, for example, be formed of a polymeric material, a glass material, or a ceramic material. In some embodiments, the reaction channel 20 is formed from PTFE. In other embodiments, the reaction channel 20 is formed from glass. The reaction channels 20 may have an inner diameter of less than or equal to about 1 mm, such as from about 1 μm to about 1.0 mm (1000 μm), from about 1 μm to about 500 μm, from about 1 μm to about 400 μm, from about 1 μm to about 300 μm, from about 1 μm to about 200 μm, from about 1 μm to about 100 μm, from about 10 μm to about 100 μm, from about 0.1 mm (100 μm) to about 1.0 mm (1000 μm), from about 0.2 mm to about 0.9 mm, from about 0.3 mm to about 0.8 mm, from about 0.4 mm to about 0.8 mm, from about 0.5 mm to about 0.8 mm, from about 0.6 mm to about 0.8 mm, or from about 0.7 mm to about 0.8 mm. A length of the reaction channels 20 may be sufficient for substantially all of the reagents to react within the reaction channels 20 and may be selected depending on the amount of GLYN to be produced and the reaction volume of the microfluidic reactor 5. The length of the reaction channels 20 may range from about 30 cm to about 400 cm.

A reaction volume of the microfluidic reactor may be less than or equal to about 20 ml, such as from about 1 μl to about 20 ml, from about 1 μl to about 100 μl, from about 1 μl to about 1000 μl, from about 5 μl to about 100 μl, from about 10 μl to about 90 μl, from about 10 μl to about 80 μl, from about 10 μl to about 50 μl, from about 100 μl to about 1000 μl, from about 1 ml to about 20 ml, from about 5 ml to about 20 ml, from about 5 ml to about 15 ml, from about 5 ml to about 10 ml, from about 10 ml to about 20 ml, from about 15 ml to about 20 ml, or from about 10 ml to about 20 ml.

The temperature control system 25 is configured to maintain the reagents in the reaction channels 20 at a desired temperature during the nitration and intramolecular condensation reactions. The temperature control system 25 may be configured to maintain the reaction channels 20 at a constant temperature during the nitration and intramolecular condensation reactions. The temperature control system 25 is also configured to dissipate heat generated by the exothermic nitration and intramolecular condensation reactions. The temperature control system 25 may, for example, be a temperature bath in which the reaction channels 20 are immersed. The microfluidic reactor 5 has a high surface area to bulk ratio, enabling quick and efficient dissipation of the heat generated by the exothermic reactions. A higher degree of temperature control may, therefore, be achieved relative to conventional processes of producing GLYN.

After conducting the intramolecular condensation reaction, the GLYN exits the second reaction channel 20 and is collected. The GLYN formed according to embodiments of the disclosure may subsequently be converted to PGN. The PGN may be used, for example, as an ingredient in a propellant, an insensitive explosive, a gas generant, etc. The PGN may be used in a rocket motor, such as a solid rocket motor, or in a warhead.

The microfluidic reactor 5 may be a commercially available continuous flow reactor, such as LABTRIX® (reaction volume 1-19.5 μl), PROTRIX® (reaction volume 1-13.5 ml), GRAMFLOW® (reaction volume up to 1 ml), KILOFLOW® (reaction volume 0.8-18 ml), PLANTRIX® (reaction volume 100 ml-4 L), from Chemtrix BV (Echt, the Netherlands). However, the microfluidic reactor 5 may be obtained from other commercial sources.

By producing the GLYN in the microfluidic reactor 5, small amounts or small volumes of the GLYN, the reagents, or any energetic intermediates are present at a particular time. Therefore, the GLYN produced according to embodiments of the disclosure may be produced more safely than conventional processes of producing GLYN. However, large amounts of the GLYN may be produced according to embodiments of the disclosure since the GLYN is produced by a continuous process. The amount of GLYN produced may be easily scaled up to production amounts, such as on the order of kilograms of GLYN. Scaleup and throughput may be increased by increasing the reaction path (e.g., the length of the reaction channels 20) or conducting reactions in parallel microfluidic reactors 5. For example, a microfluidic reactor 5 having a 5 μl reaction volume may produce up to about 50 g of GLYN per day. A microfluidic reactor 5 having a 200 μl reaction volume may produce production amounts of GLYN, such as between about 6 L/hour and about 12 L/hour.

Producing the GLYN in the microfluidic reactor 5 also enables good heat transfer during the exothermic reactions, so the potential for run-away reactions is greatly reduced and the safety of producing the GLYN is increased. Safety is also increased because the continuous process may be conducted remotely, which also reduces risks to personnel, facilities, and equipment and reduces operation costs. By controlling the reaction temperatures of the nitration reaction and the intramolecular ring closure reaction in the microfluidic reactor 5, the nitrated glycerol compound and the GLYN may also be produced at higher purities by decreasing side reactions.

The following examples serve to explain embodiments of the disclosure in more detail. These examples are not to be construed as being exhaustive or exclusive as to the scope of this disclosure.

EXAMPLES

Example 1

Microfluidic Reactor

A microfluidic reactor including syringe pumps, tubing, a T-joint, a resonance tube, and a temperature bath was constructed. The microfluidic reactor was similar to the schematic in FIG. 2, except that a single reaction channel was present. Two syringe pumps were connected to the T-joint with tubing to introduce reagents to the microfluidic reactor. The syringe pumps were set to constant flow rates. The tubing was acid-resistant PTFE tubing and had an inner diameter of 0.031 inch-0.039 inch (0.79 mm-1.0 mm). The T-joint was an ethylene-tetrafluoroethylene (TEFZEL®) T-joint and included two inlet ports and one outlet port. The tubing was used to introduce the reagents to the T-joint to enable mixing of the reagents as the reagents entered the resonance tube. The resonance tube was varied in length, between 30 cm and 412 cm depending on the process conditions. To provide temperature control, the resonance tube was coiled and submerged in a temperature bath, which was controllable to be a constant temperature. Reagent feed ratios were controlled using different syringe sizes, dilution of the reagents, or by using separate syringe pumps set to desired flow rates. Resonance time was controlled by the resonance tube length and/or the combined flow rate of reagents.

Example 2

Glycerol Nitration

Glycerol and nitric acid or a nitric acid solution were injected into the microfluidic reactor described in Example 1. The glycerol and nitric acid were reacted at different process conditions and the reaction products were collected from the terminal end of the resonance tube and analyzed by nuclear magnetic resonance (NMR) spectroscopy. The reaction products were measured without workup. Table 1 includes the process variables (reaction temperature, nitric acid concentration, ratio of nitric acid:glycerol, flow rate of the glycerol and nitric acid, resonance time) and the conversion results, which are expressed in mole percent (mol %) of the glycerol, DNG compound, MNG compound, and NG.

required. To increase the reaction time, the resonance tube was extended for the remaining experiments. The data also showed that higher nitric acid concentrations increased the conversion to DNG. However, high nitric acid concentrations also increased the amount of NG produced. As shown in Table 1, Experiments 11 and 12 resulted in the high conversions of glycerol to DNG with minimal MNG. However, Experiment 11 resulted in a significant amount of NG. Experiment 12 was duplicated as Experiment 12b to demonstrate repeatability. The percent conversion and amount of NG present in Experiments 12 and 12b were determined to be in the same ranges expected for a conventional batch reaction. The nitration reaction conditions in Experiments 7 and 9-12b produced DNG at greater than or equal to 50 mol %.

Figure 3:
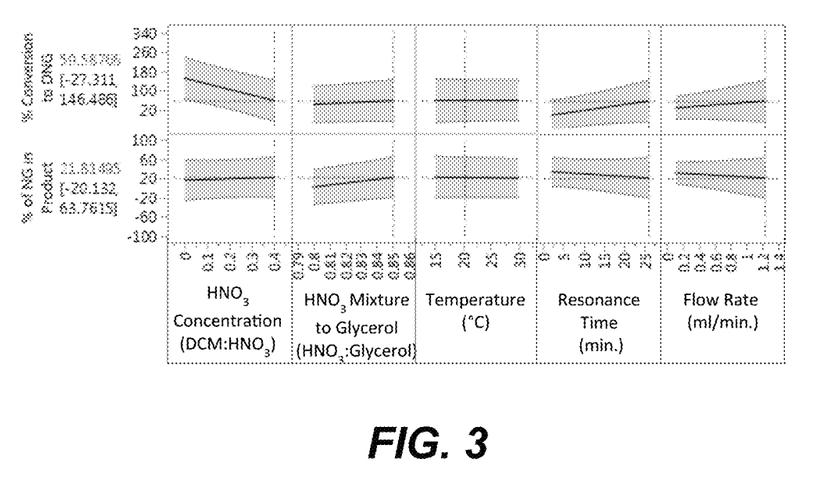
FIG. 3 is a graph showing statistical analysis of glycerol conversion to a dinitroglycerol (DNG) compound and trinitroglycerol (NG) as a function of different process variables.

Statistical analysis of the glycerol conversion was conducted using JMP software to determine the effects of changing the process variables. Results of the statistical analysis are shown in FIG. 3. The statistical analysis showed the nitric acid concentration being the most significant factor, with nitric acid solutions including higher nitric acid concentrations (lower solvent amounts) providing increased conversion of glycerol to DNG.

Example 3

DNG Intramolecular Condensation

An acidic organic solution of DNG and a sodium hydroxide (NaOH) solution were injected into the microfluidic reactor described in Example 1. The DNG solution was prepared separately using a batch reaction set-up. The DNG and NaOH solution were reacted at different process conditions and the reaction products were collected and analyzed by NMR. The reaction products were measured with some workup. Table 2 includes the process variables (ratio of DNG:NaOH, reaction temperature, flow rate, resonance

TABLE 1

Glycerol Nitration Test Matrix and Results

| Exp | Temp (° C.) | Acid Concentration (DCM:HNO$_3$) | Acid: Glycerol (Volume ratio) | Reaction Channel Length (mm) | Flow Rate (ml/min) | Resonance Time (min) | % Conversion From Glycerol | | | |
|---|---|---|---|---|---|---|---|---|---|---|
| | | | | | | | DNG (mol %) | MNG (mol %) | NG (mol %) | Glycerol (mol %) |
| 1 | 15 | 2:3 | 4:1 | 300 | 0.11 | 2.05 | 0 | 0 | 0 | 100 |
| 2 | 25 | 2:3 | 4:1 | 300 | 0.11 | 2.05 | 0 | 0 | 0 | 100 |
| 3 | 30 | 2:3 | 4:1 | 1200 | 0.11 | 8.57 | 0 | 0 | 0 | 100 |
| 4 | 20 | 1:3 | 4:1 | 4120 | 0.15 | 21.60 | 26 | 26 | 1 | 46 |
| 5 | 20 | 1:5 | 4:1 | 4120 | 1.23 | 2.68 | 13 | 25 | 2 | 53 |
| 6 | 20 | 1:5 | 4:1 | 4120 | 0.25 | 13.40 | 12 | 48 | 0 | 40 |
| 7 | 20 | 1:5 | 4:1 | 4120 | 0.13 | 26.0 | 61 | 22 | 6 | 11 |
| 8 | 27 | 1:5 | 4:1 | 4120 | 1.23 | 2.68 | 29 | 31 | 1 | 39 |
| 9 | 20 | 0:1 | 4:1 | 4120 | 1.23 | 2.68 | 67 | 16 | 11 | 6 |
| 10 | 20 | 0:1 | 4:1 | 4120 | 0.25 | 13.40 | 51 | 31 | 3 | 15 |
| 11 | 20 | 0:1 | 4:0.68 | 4120 | 0.76 | 4.23 | 57 | 6 | 35 | 2 |
| 12 | 20 | 0:1 | 4:0.68 | 4120 | 0.15 | 21.0 | 71 | 14 | 10 | 5 |
| 12b | 20 | 0:1 | 4:0.68 | 4120 | 0.152 | 21.0 | 72 | 13 | 10 | 5 |

Experiments 1-3 did not show conversion of the glycerol, and it was determined that longer reaction times were time) that were tested and the conversion results, which are expressed in mole percent (mol %) of the reaction products.

TABLE 2

Conversion of DNG to GLYN Test Matrix and Results

| Exp | DNG: NaOH[a] (Volume Ratio) | Temperature (° C.) | Reaction Channel Length (mm) | Flow Rate (ml/min) | Resonance Time (min) | Conversion Mol % Side Products | Mol % GLYN | Mol % DNG |
|---|---|---|---|---|---|---|---|---|
| 1 | 4:1 | 14 | 825 | 0.57 | 1.13 | 0 | 20 | 80 |
| 2 | 4:1 | 14 | 825 | 0.11 | 5.65 | 0 | 20 | 80 |
| 3 | 2.7:1 | 14 | 825 | 0.63 | 1.02 | 1 | 82 | 17 |
| 4 | 2.7:1 | 14 | 825 | 0.13 | 5.10 | 3 | 90 | 8 |
| 5 | 2.7:1 | 20 | 825 | 0.63 | 1.02 | 2 | 93 | 5 |
| 6 | 2.7:1 | 20 | 825 | 0.13 | 5.10 | 4 | 93 | 3 |
| 7 | 2.7:1 | 20 | 4120 | 0.63 | 5.10 | 5 | 95 | 0 |
| 8 | 2.7:1 | 20 | 4120 | 0.31 | 10.44 | 9 | 91 | 0 |
| 9 | 2.7:1 | 20 | 4120 | 0.13 | 25.0 | 40 | 60 | 0 |
| 10 | 2.7:1 | 20 | 4120 | 0.95 | 2.50 | 6 | 87 | 7 |
| 11[b] | 2.7:1 | 20 | 4120 | 0.63 | 5.10 | 13 | 84 | 3 |

[a]DNG is 2.48M in $HNO_3$ and NaOH is 7.2M in water
[b]Exp 11 is a duplicate run of Exp 7

The chemical transformation to GLYN proved much easier in the microfluidic reactor than the nitration reaction, with up to 100% reaction of the DNG compound achieved. It was also noted during the experiments that the microfluidic reactor isothermal bath remained stable, with no observed temperature rise. This indicated that the intramolecular condensation reaction involved the neutralization of excess nitric acid from the nitration reaction, which is an extremely exothermic reaction. The conversion of the DNG compound to GLYN was greater than or equal to about 85 mol %, such as greater than or equal to about 90 mol % or greater than or equal to about 95 mol %.

Figure 4:
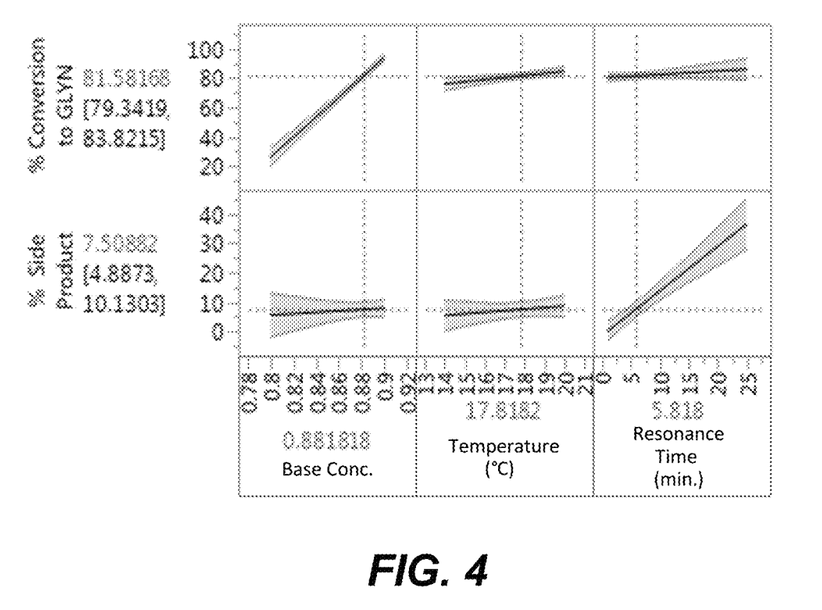
FIG. 4 is a graph showing statistical analysis of DNG compound conversion to GLYN as a function of different process variables.

Statistical analysis of the glycidyl nitrate conversion was conducted using JMP software to determine the effects of changing the process variables. The statistical analysis showed that the concentration of the NaOH, resonance time, and temperature were important factors. The prediction model based on this analysis showed that maximizing NaOH concentration increased GLYN conversion, with little impact on the amount of side products produced. Also, increasing the temperature provided minor improvements in the GLYN conversion and a lower resonance time lowered the amount of side products. Results of the statistical analysis are shown in FIG. 4.

Example 4

Microfluidic Reactor

A microfluidic reactor including three syringe pumps, tubing, two T-joints, two resonance tubes, and two temperature baths was constructed, similar to the schematic in FIG. 2. Two syringe pumps were connected to a first T-joint with tubing to introduce glycerol and nitric acid to the microfluidic reactor. The syringe pumps were set to constant flow rates. The tubing was acid-resistant PTFE tubing and had an inner diameter of 0.031 inch-0.039 inch (0.79 mm-1.0 mm). The first T-joint was a TEFZEL® T-joint and included two inlet ports and one outlet port. The tubing was used to flow the glycerol and nitric acid through respective inlets to the first T-joint, enabling mixing of the glycerol and nitric acid as the glycerol and nitric acid enter a first resonance tube. The first resonance tube was 412 cm in length. To provide temperature control, the first resonance tube was coiled and submerged in a first temperature bath, which was maintained at a temperature of 22° C. The first resonance tube was connected to an inlet of a second T-joint, which was a TEFZEL® T-joint and included two inlet ports and one outlet port. A third syringe pump was connected to the other inlet of the second T-joint and sodium hydroxide was introduced to the second T-joint. The second T-joint enabled mixing of the sodium hydroxide and reaction product from the first resonance tube. A second resonance tube having a length of 384 cm was connected to the outlet port of the second T-joint.

Example 5

Glycerol Nitration and DNG Intramolecular Condensation

The nitration and intramolecular condensation reactions were performed in series in the microfluidic reactor described in Table 4. Glycerol and nitric acid were injected into the T-joint under the process conditions discussed in Example 2 to produce DNG. The resonance tube containing DNG was then plumbed directly into the second T-joint where the DNG was mixed with NaOH and chemically transformed to GLYN. The glycerol and nitric acid were reacted at different process conditions and the reaction products were collected and analyzed by NMR. The specific process conditions and results for each of the reactions are shown in Tables 3-5. Table 3 includes the process variables (ratio of acid:glycerol, reaction temperature, flow rate, resonance time) that were tested for the nitration reaction and Table 5 includes the conversion results, which are expressed in mole percent (mol %) of the reaction products. The DNG and NaOH solution were reacted at different process conditions and the reaction products were collected and analyzed by NMR. Table 4 includes the process variables (NaOH concentration, temperature, flow rate, resonance time) that were tested and Table 5 includes the conversion results, which are expressed in mole percent (mol %) of the reaction products.

TABLE 3

Nitration Process Conditions

| Experiment | HNO$_3$:Glycerol | Temperature (° C.) | Flow Rate (ml/min) | Resonance Time (min) |
|---|---|---|---|---|
| 1 | 4:0.68 | 21 | 0.76 | 4.26 |
| 2 | 4:0.68 | 22 | 0.76 | 4.26 |
| 3 | 4:0.68 | 22 | 0.38 | 8.51 |

TABLE 4

Intramolecular Condensation Process Conditions

| Experiment | NaOH Concentration | Temperature (° C.) | NaOH Flow Rate (mL/min) | Resonance Time (min) |
|---|---|---|---|---|
| 1 | 3.4 | 22 | 0.77 | 1.97 |
| 2 | 7.2 | 22 | 0.77 | 1.97 |
| 3 | 7.2 | 32 | 2.40 | 1.08 |

TABLE 5

Results From Glycerol Nitration and DNG Intramolecular Condensation

| Experiment | DNG (mol %) | MNG (mol %) | NG (mol %) | Glycerol (mol %) | GLYN (mol %) | Side Product (mol %) | Notes |
|---|---|---|---|---|---|---|---|
| 1 | N/A | N/A | N/A | N/A | N/A | N/A | Insufficient base |
| 2 | N/A | N/A | N/A | N/A | N/A | N/A | Inorganic precipitates |
| 3 | 12% | 1% | 21% | 0% | 58% | 8% | N/A |

GLYN was produced at a greater than about 58 mol % conversion from starting material. It is likely that additional optimization of the process conditions would further increase the reaction yield. The caustic induced transformation of DNG performed in the microfluidic reactor gave a high conversion to GLYN. Therefore, GLYN was successfully produced at a reasonable level of conversion.

While the disclosure is susceptible to various modifications and alternative forms, specific embodiments have been shown by way of example in the drawings and have been described in detail herein. However, the disclosure is not intended to be limited to the particular forms disclosed. Rather, the disclosure encompasses all modifications, equivalents, and alternatives falling within the scope of the disclosure as defined by the following appended claims and their legal equivalents.

What is claimed is:

1. A method of producing glycidyl nitrate, comprising:
reacting glycerol and nitric acid in a microfluidic reactor to form a nitrated glycerol compound, a reaction volume of the microfluidic reactor comprising less than about 20 ml and an inner diameter of a reaction channel of the microfluidic reactor of less than or equal to about 1000 μm; and
reacting the nitrated glycerol compound with a base in the microfluidic reactor to form glycidyl nitrate.

2. The method of claim 1, wherein reacting glycerol and nitric acid in a microfluidic reactor comprises continuously introducing the glycerol and nitric acid into the microfluidic reactor.

3. The method of claim 1, wherein reacting the nitrated glycerol compound with a base in the microfluidic reactor comprises continuously introducing the nitrated glycerol compound and the base into the microfluidic reactor.

4. The method of claim 1, wherein reacting glycerol and nitric acid in a microfluidic reactor to form a nitrated glycerol compound comprises reacting the glycerol and nitric acid without a solvent.

5. The method of claim 1, wherein reacting glycerol and nitric acid in a microfluidic reactor to form a nitrated glycerol compound comprises reacting a total volume of less than 1 ml of the glycerol and nitric acid in the microfluidic reactor.

6. The method of claim 1, further comprising recovering the glycidyl nitrate.

7. The method of claim 6, wherein recovering the glycidyl nitrate comprises recovering the glycidyl nitrate at a conversion of greater than about 50 mol %.

8. The method of claim 1, wherein reacting glycerol and nitric acid in a microfluidic reactor comprises reacting the glycerol and nitric acid in a reaction volume of from about 100 μl to about 1000 μl.

9. A method of producing glycidyl nitrate, comprising:
introducing glycerol and nitric acid into a first reaction channel of a microfluidic reactor comprising a reaction volume of less than about 20 ml and an inner diameter of a reaction channel of the microfluidic reactor of less than or equal to about 1000 μm;
reacting the glycerol and nitric acid in the first reaction channel to form a nitrated glycerol compound;
reacting the nitrated glycerol compound with sodium hydroxide in a second reaction channel of the microfluidic reactor to form glycidyl nitrate; and
recovering the glycidyl nitrate.

10. The method of claim 9, wherein introducing glycerol and nitric acid into a first reaction channel of a microfluidic reactor comprises introducing the glycerol and nitric acid into a first reaction channel comprising internal dimensions between about 1 μm and about 1000 μm.

11. The method of claim 9, wherein reacting the glycerol and nitric acid in the first reaction channel comprises reacting the glycerol and nitric acid in the first reaction channel without dichloromethane.

12. The method of claim 9, wherein reacting the glycerol and nitric acid in the first reaction channel comprises reacting the glycerol with concentrated nitric acid in the first reaction channel.

13. The method of claim 9, wherein reacting the glycerol and nitric acid in the first reaction channel to form a nitrated glycerol compound comprises forming a dinitroglycerol compound comprising 1,2-dinitroglycerol, 1,3-dinitroglycerol, or combinations thereof.

14. A method of producing glycidyl nitrate, comprising:
continuously reacting glycerol and nitric acid in a first reaction channel of a microfluidic reactor to form a dinitroglycerol compound, the microfluidic reactor comprising a reaction volume of less than about 20 ml and an inner diameter of a reaction channel of the microfluidic reactor of less than or equal to about 1000 μm; and continuously reacting the dinitroglycerol compound with sodium hydroxide in a second reaction channel of the microfluidic reactor to form glycidyl nitrate; and recovering the glycidyl nitrate.

15. The method of claim 14, wherein continuously reacting glycerol and nitric acid in a first reaction channel of a microfluidic reactor to form a nitrated glycerol compound comprises forming the nitrated glycerol compound at greater than or equal to about 50 mole percent.

16. The method of claim 14, wherein continuously reacting glycerol and nitric acid in a first reaction channel of a microfluidic reactor to form a nitrated glycerol compound comprises reacting the glycerol and nitric acid at a temperature of from about 20° C. to about 25° C.

17. The method of claim 14, wherein continuously reacting glycerol and nitric acid in a first reaction channel of a microfluidic reactor to form a nitrated glycerol compound comprises reacting the glycerol and nitric acid in a first reaction channel comprising at least one dimension between about 1 μm and about 1000 μm.

18. The method of claim 14, wherein recovering the glycidyl nitrate comprises producing at least 1 kilogram of the glycidyl nitrate.

* * * * *